United States Patent
Gaussem et al.

(10) Patent No.: US 9,909,977 B2
(45) Date of Patent: Mar. 6, 2018

(54) SIMULTANEOUS MONITORING OF FIBRINOGEN AND HAEMATOCRIT IN WHOLE BLOOD

(71) Applicants: INSTITUT NATIONAL DE LA SANTE ET DE LA RECHERCHE MEDICALE, Paris (FR); ETAT FRANCAIS (MINISTERE DE LA DEFENSE), SERVICE DE SANTE DES ARMEES, Paris (FR); ASSISTANCE PUBLIQUE—HOPITAUX DE PARIS, Paris (FR); UNIVERSITE PARIS DESCARTES, Paris (FR)

(72) Inventors: Pascale Gaussem, Paris (FR); Anne Godier, Paris (FR); Isabelle Gouin-Thibault, Paris (FR); Bernard Le Bonniec, Paris (FR); Anne-Celine Martin, Paris (FR); Nyoucha Morravedge, Paris (FR); Marc Samama, Paris (FR)

(73) Assignees: INSTITUT NATIONAL DE LA SANTE ET DE LA RECHERCHE MEDICAL, Paris (FR); ETAT FRANCAIS (MINISTERE DE LA DEFENSE), SERVICE DE SANTE DES ARMEES, Paris (FR); ASSITANCE PUBLIQUE—HOPITAUX DE PARIS, Paris (FR); UNIVERSITE PARIS DECARTES, Paris (FR)

( * ) Notice: Subject to any disclaimer, the term of this patent is extended or adjusted under 35 U.S.C. 154(b) by 0 days.

(21) Appl. No.: 15/029,266

(22) PCT Filed: Oct. 15, 2014

(86) PCT No.: PCT/IB2014/065337
§ 371 (c)(1),
(2) Date: Apr. 14, 2016

(87) PCT Pub. No.: WO2015/056190
PCT Pub. Date: Apr. 23, 2015

(65) Prior Publication Data
US 2016/0238521 A1    Aug. 18, 2016

(30) Foreign Application Priority Data
Oct. 16, 2013    (EP) .................................... 13306418

(51) Int. Cl.
G01N 33/86    (2006.01)
G01N 21/31    (2006.01)
G01N 33/50    (2006.01)
G01N 33/80    (2006.01)
G01N 21/3577  (2014.01)
G01N 33/49    (2006.01)
G01N 21/17    (2006.01)

(52) U.S. Cl.
CPC ......... G01N 21/31 (2013.01); G01N 21/3577 (2013.01); G01N 33/49 (2013.01); G01N 33/5002 (2013.01); G01N 33/80 (2013.01); G01N 33/86 (2013.01); G01N 2021/1748 (2013.01); G01N 2201/061 (2013.01); G01N 2333/75 (2013.01)

(58) Field of Classification Search
None
See application file for complete search history.

(56) References Cited

U.S. PATENT DOCUMENTS

| | | | | |
|---|---|---|---|---|
| 5,506,145 A | * | 4/1996 | Bull .................. | C12Q 1/56 210/782 |
| 5,567,869 A | * | 10/1996 | Hauch ................ | G01N 21/59 128/DIG. 22 |
| 8,053,239 B2 | * | 11/2011 | Wheeler .............. | C07K 1/30 204/451 |
| 2009/0311736 A1 | * | 12/2009 | Ciotti ................ | G01N 15/05 435/29 |
| 2010/0087633 A1 | | 4/2010 | Wheeler et al. | |

FOREIGN PATENT DOCUMENTS

CN    104049089    *    9/2014
WO    2012/087633 A1    2/2012

OTHER PUBLICATIONS

Mackie I. et al. Guidelines on Fibrinogen Assays. British J of Haematology 121:396-404, 2003.*
Woodward M. et al. Does Sticky Blood Predict a Sticky End? . . . British J of Haematology 122:645-650, 2003.*
'Einzigartige Flexibitaet in der Molekuelspektroskopie', Feb. 11, 2013, Analytik-Jena, Web.
"Mein SPECORD", Feb. 20, 2013, Analytik-Jena, Web.
"Specord Plus", Jan. 18, 2013, Analytik-Jena, Web.
Godal et al., "Gelation of Soluble Fibrin in Plasma by Ethanol", Scandinavian Journal of Haematology, Dec. 1, 1966, pp. 342-350, vol. 3, No. 5.
G. Palareti, "Fibrinogen Assays: a Collaborative Study of Six Different Methods", Clin Chem, Jan. 1, 1991, p. 197.
Exner et al., "An evaluation of currently available methods for plasma fibrinogen", American Journal of Clinical Pathology, May 1, 1979, pp. 521-527, vol. 71, No. 5.
Desvignes et al., "Direct determination of plasma fibrinogen levels by heat precipitation. A comparison of the technique against thrombin clottable fibrinogen with spectrophotometry and radial immunodiffusion", Clinical Chimica Acta, Feb. 19, 1981, pp. 9-17, vol. 110, No. 1.

(Continued)

Primary Examiner — Ralph J Gitomer
(74) Attorney, Agent, or Firm — Whitham, Curtis & Cook, P.C.

(57) ABSTRACT

The present invention relates to a method for determining both (a) the haematocrit value and (b) the fibrinogen content in whole blood of an individual in less than 5 minutes, as well as to associated portable apparatus.

12 Claims, 4 Drawing Sheets

(56) References Cited

OTHER PUBLICATIONS

Figure 1:
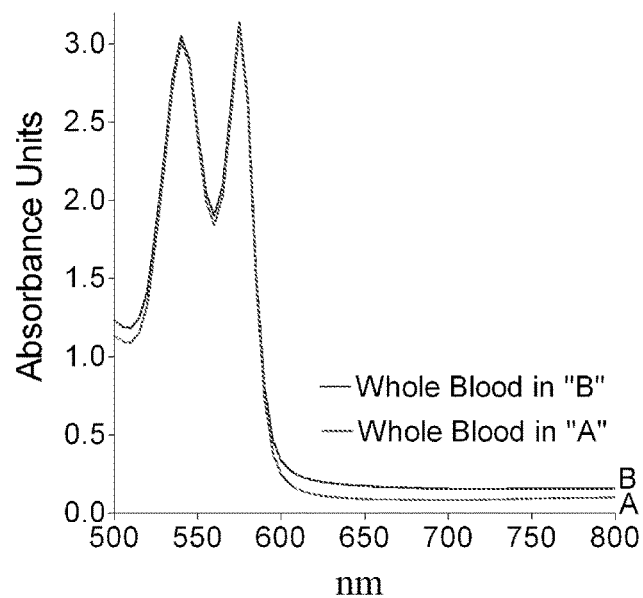

Amukele et al., "Comparison of Plasma with Whole Blood Prothrombin Time and Fibrinogen on the Same Instrument", American Journal of Clinical Pathology, Mar. 15, 2010, pp. 550-556, vol. 133, No. 4.

Matsuda et al., "Relationship between fibrinogen and blood viscosity", Thrombosis Research, May 1, 1976, pp. 25-33, vol. 8.

* cited by examiner

US 9,909,977 B2

SIMULTANEOUS MONITORING OF FIBRINOGEN AND HAEMATOCRIT IN WHOLE BLOOD

FIELD OF THE INVENTION

The present invention relates to a method, and associated devices, for rapidly monitoring fibrinogen content, and in particular both fibrinogen content and haematocrit in the whole blood of an individual.

More particularly, the present invention relates to a method, and associated devices, allowing simultaneous evaluation within minutes of haematocrit and fibrinogen content of an individual, based only on a very small amount of whole blood of said individual.

BACKGROUND OF THE INVENTION

Fibrinogen is one of the major coagulation factors in the vertebrates.

Measure of its content in an individual can provide different information and/or be the function of many variables. For example, fibrinogen level is increased in case of acute phase reaction or in post-menopausal women, and also increases with ageing, pregnancy or oral contraception. On the contrary, fibrinogen level is decreased in case of liver diseases, inherited deficiencies such as hypofibrinogenaemia and dysfibrinogenaemia, disseminated intravascular coagulopathy or during massive bleeding.

More particularly, due to its essential role in blood clotting, the fibrinogen content of an individual suffering or likely to suffer of a severe haemorrhage needs to be evaluated as fast as possible, notably as it is an early predictor of outcome. The result obtained, as well as the measurement of the haematocrit of the individual, are critical information for determining whether this individual has developed a coagulopathy and needs to receive immediately coagulation factors supplement and/or massive transfusion. Thus, fibrinogen concentration appears as a trigger for initiating replacement as well as for a treatment goal.

Indeed, a low concentration of fibrinogen in the blood can be associated with an increase of the risk of haemorrhage and/or an increase of the on-going bleeding. Moreover, it has been demonstrated that in case of haemorrhage, fibrinogen is the first coagulation factor to reach critical level. This decrease is mostly due to its conversion into fibrin by thrombin during blood clot formation.

Several methods well known in the art are already available to estimate fibrinogen content in plasma. Mention can be made of the Prothrombin Time-derived fibrinogen assay, in which Prothrombin Time is determined by optical density change for a range of plasma dilutions with known fibrinogen levels, and the result is obtained on a reference curve. Well known immunological assays are also used, such as ELISA assay, radial immunodiffusion or electrophoresis. Different gravimetric assays, comprising Jacobsson's method, are also commonly used and are based on the formation of a clot by addition of thrombin or reptilase in excess before washing, drying then weighting the obtained clot. An alternative consists in dissolving the clot after its formation in an urea-alkaline solution then performing spectrophotometry in order to determine the concentration of fibrin through its extinction coefficient, considering that all the fibrinogen has been converted in fibrin and that the clot is only constituted of said fibrin.

Nowadays, the most commonly used method for determining fibrinogen content in an individual is the Clauss method. This method is carried out on diluted plasma, and consists in measuring the time to clot formation following addition of an excess of thrombin (typically 100 U/ml), so that the clotting time is independent of the thrombin concentration. Time to clot is detected photometrically by means of turbidity increase or mechanically through the cease of movement resulting from the gelation using a signal provided by a magnetic rod or added particles (Oberhadt et al., Clin. Chem. (1991), 37:520-526). A reference curve allows deducing the fibrinogen content as a function of the time to clot formation.

However, these methods are usually carried out on plasma in a laboratory. Then, they all require first separating it from the whole blood of the individual to be tested by centrifugation before performing the fibrinogen content assay.

Moreover, if the gravimetric assays can be considered as being more accurate than the Clauss method, it requires at least 2 hours to provide a result, whereas the Clauss method still necessitates 20 minutes including plasma separation. It can further be noted that these methods necessitate the use of a bulky and expensive equipment. These methods are also time consuming and are not accurate in case of massive bleeding.

Hence, in the field of emergency care, there is a need for a method appropriate for the assessment within minutes of bleeding risks and in the therapeutic management of bleeding based on the measure of fibrinogen level.

Also, there is a need for a method allowing within minutes the detection of an alarming fibrinogen level and in particular less than 1.5 g/L.

Moreover, there is a fundamental need to develop a method that can provide within minutes, in particular in less than 5 minutes, more particularly within 3 minutes, a sufficiently reliable result based on the measure of fibrinogen level to determine if an individual needs to receive coagulation factors supplement and/or to be transfused.

There is further a need for a method only necessitating a transportable material, in particular in an ambulance or any emergency rescue vehicle, or that can even be transportable by rescuers and emergency care personnel, for example in a specialised suitcase or backpack.

Furthermore, as all the methods used to date by care professionals were based on plasma fibrinogen content, the reference values concerning fibrinogen level are internationally based on plasma fibrinogen content. There is thus a need for a method based on a whole blood sample instead of plasma, combined with a mean to transcribe the results obtained in plasma fibrinogen content.

Consequently, there is a need for a method allowing within minutes to determine both haematocrit and fibrinogen content in whole blood of an individual.

Haematocrit is the percentage of red blood cells in the whole blood of an individual. Measure of its level in an individual can provide different information. For example, an increase of haematocrit is found in people suffering from dehydration, oxygen deprivation or polycythemia. On the contrary, a decrease of the haematocrit occurs during anaemia. Anaemia can result from different causes, such as cancer, cirrhosis or vitamin deficiency, but is also a sign of blood loss, and as such internal bleeding.

SUMMARY OF THE INVENTION

The present invention aims to meet the here-above indicated needs.

It has been found herein that an haematocrit value and a fibrinogen content of a whole blood sample may be determined by using a method comprising a step wherein fibrinogen is precipitated by using a precipitant consisting of a water-soluble organic solvant.

According to one of its objects, the present invention relates to a method for determining both (a) the haematocrit value and (b) the fibrinogen content in whole blood of an individual comprising:

(i) mixing a given volume of whole blood sample from the individual with a liquid solution, wherein the liquid solution comprises a low ionic strength buffer as well as a precipitant, and wherein the content of the precipitant ranges from 0.5 to 40% by weight based on the total weight of the solution, whereby a test mixture is obtained, the precipitant being selected from the group consisting of a ($C_1$-$C_6$)alcohol, acetaldehyde, acetic acid, acetone, acetonitrile, 2-butoxyethanol, butyric acid, diethanolamine, diethylenetriamine, dimethylformamide, dimethoxyethane, dimethyl sulfoxide, 1,4-dioxane, ethylamine, ethylene glycol, formic acid, furfuryl alcohol, methyl diethanolamine, methyl isocyanide, propanoic acid, pyridine and tetrahydrofuran;

(ii) incubating the test mixture during 30 seconds or more;

(iii) measuring light absorbance of the test mixture obtained at the end of step (ii) at a wavelength ranging from 520 to 590 nanometers whereby an absorbance value A is obtained;

(iv) measuring light absorbance of the test mixture obtained at the end of step (ii) at a wavelength ranging from 650 to 850 nanometers, whereby an absorbance value B is obtained;

(v) determining the haematocrit value of the individual by comparing the absorbance value A obtained at step (iii) with an haematocrit reference value; and (vi) determining the fibrinogen content in the whole blood of the individual by comparing the absorbance value B obtained at step (iv) with a fibrinogen content reference value;

wherein the liquid solution used at step (i) and the test mixture used at steps (ii) to (iv) are maintained at a desired temperature, the desired temperature being selected in a temperature range of from 4 to 40° C.

This method preferentially further comprises step (vii) of extrapolating a fibrinogen content value in the plasma of the individual using the haematocrit value obtained at step (v) and the fibrinogen content in the whole blood determined at step (vi).

Indeed, the inventors have unexpectedly found that a method according to the invention allows determining both the haematocrit value and the fibrinogen content in whole blood of an individual within minutes, in particular in less than 3 minutes, more particularly in between 60 seconds and 180 seconds, which encompasses in about 90 seconds, after the whole blood sample collection. Moreover, a method according to the invention allows transcribing the results obtained in whole blood in plasma fibrinogen content. Indeed, due to the absence of fibrinogen in red blood cells, the fibrinogen content in whole blood is always lower than the fibrinogen content in plasma.

The methods of the invention are more particularly based on the findings that kinetic of fibrinogen precipitation is a function of three different elements: (i) the temperature, (ii) the nature of the precipitant and (iii) the amount of precipitant.

Indeed, increasing the amount of precipitant accelerates fibrinogen precipitation. On the contrary, increasing the temperature slows fibrinogen precipitation down. Furthermore, not all the precipitants are capable of efficiently precipitating fibrinogen. It was thus necessary to find the adequate balance in order to obtain the intended results.

Another problem when considering a method according to the invention lies in the fact that detection of the fibrinogen precipitate in a whole blood sample is very difficult without prior or simultaneous disruption of the red blood cells, more particularly when considering the fact that most precipitants trigger agglutination of red blood cells and thus disturb their lysis.

For instance, within the Hofmeister series, ammonium sulfate precipitant permits efficient fibrinogen evaluation in plasma, but results in cell agglutination in whole blood render unfeasible the measure of fibrinogen content by selective precipitation. The same seems true with other "salting out" reagents acting by dehydration. Further addition of ionic or nonionic detergent such as Triton, NP-40, Tween, or SDS failed solving the problem probably due to the high ionic strength required for effective dehydration of fibrinogen. Addition of "salting in" chaotropic agents such as urea or guanidinium chloride also proves to be ineffective for simultaneous cell lyses and fibrinogen precipitation. Finally, SDS-NaOH alkaline solution also triggers agglutination of red blood cells.

The inventors have unexpectedly managed to determine conditions allowing, in a very short time period, e.g. of less than 3 minutes, for:

precipitating all the fibrinogen contained in a whole blood sample;

disrupting red blood cells contained in the said sample;

determining haematocrit value as well as whole blood fibrinogen content; and extrapolating the fibrinogen content value in the plasma.

As used herein, the terms "fibrinogen content", "fibrinogen value" and "fibrinogen content value" are synonyms used to indicate the amount of fibrinogen present either in plasma or in whole blood of a sample previously collected from an individual.

An "individual" or a "patient" considered within the present invention is a mammal, and more preferably an animal of economic importance which encompasses primarily human individuals as well as farms, laboratories or food industries animals, such as sheep, swine, cattle, goats, dogs, cats, horses, poultry, mice, rats. Most preferably, an individual is a human. Preferably, an individual according to the invention is suffering or likely to suffer of a haemorrhage.

According to another of its aspects, the invention relates to a method for determining both (a) the haematocrit value and (b) the fibrinogen content in whole blood of an individual comprising the steps of:

(i-a) mixing a given volume of a first whole blood sample from an individual with a first liquid solution, wherein the first liquid solution comprises a low ionic strength buffer as well as a precipitant, and wherein the content of the precipitant ranges from 0.5 to 20% by weight based on the total weight of the solution, whereby a first test mixture is obtained, the precipitant being selected from the group consisting of a ($C_1$-$C_6$)alcohol, acetaldehyde, acetic acid, acetone, acetonitrile, 2-butoxyethanol, butyric acid, diethanolamine, diethylenetriamine, dimethylformamide, dimethoxyethane, dimethyl sulfoxide, 1,4-dioxane, ethylamine, ethylene glycol, formic acid, furfuryl alcohol, methyl diethanolamine, methyl isocyanide, propanoic acid, pyridine and tetrahydrofuran;

(ii-a) mixing another given volume of a second whole blood sample from the individual with a second liquid solution, wherein the second liquid solution comprises a low ionic strength buffer as well as a precipitant, and wherein the content of the precipitant ranges from 20 to 40% by weight based on the total weight of the solution, whereby a second test mixture is obtained, the precipitant being selected from the group consisting of a $(C_1\text{-}C_6)$alcohol, acetaldehyde, acetic acid, acetone, acetonitrile, 2-butoxyethanol, butyric acid, diethanolamine, diethylenetriamine, dimethylformamide, dimethoxyethane, dimethyl sulfoxide, 1,4-dioxane, ethylamine, ethylene glycol, formic acid, furfuryl alcohol, methyl diethanolamine, methyl isocyanide, propanoic acid, pyridine and tetrahydrofuran;

(iii-a) incubating the first and second test mixtures during 30 seconds or more;

(iv-a) measuring light absorbance of the first test mixture obtained at the end of step (iii-a) at a wavelength ranging from 520 to 590 nanometers, whereby an absorbance value A is obtained;

(v-a) measuring light absorbance of the second test mixture obtained at the end of step (iii-a) at a wavelength ranging from 650 to 850 nanometers, whereby an absorbance value B is obtained;

(vi-a) determining the haematocrit value of the individual by comparing the absorbance value A obtained at step (iv-a) with an haematocrit reference value; and (vii-a) determining the fibrinogen content in the whole blood of the individual by comparing the absorbance value B obtained at step (v-a) with fibrinogen content reference value;

wherein the first and second liquid solutions used at steps (i-a) and (ii-a) and the first and second test mixtures used at steps (iii-a) to (v-a) are each independently maintained at a desired temperature, the desired temperature being selected in a temperature range of from 4 to 40° C.

Advantageously, this method further comprises step (viii-a) of determining a fibrinogen content value in the plasma of the individual using the haematocrit value obtained at step (vi-a) and the fibrinogen content in the whole blood determined at step (vii-a).

According a preferred embodiment, the absorbance value A is measured in a method according to the invention at a wavelength of 560 nm.

According to a preferred embodiment, the absorbance value B is measured in a method according to the invention at a wavelength of 710 nm.

According to a preferred embodiment, the first liquid solution comprises ethanol in a content of 10% by weight based on the total weight of the solution and the desired temperature is 30° C.

According to a preferred embodiment, the second liquid solution comprises ethanol in a content of 30% by weight based on the total weight of the solution and the desired temperature is 30° C.

According to another of its aspects, the invention relates to an apparatus for determining both (i) the haematocrit value and (ii) the fibrinogen content value in whole blood of an individual, comprising:

(i) a light source configured to emit at least one of:
 (1) a first wavelength ranging from 520 to 590 nanometers, and
 (2) a second wavelength ranging from 650 to 850 nanometers;

(ii) a photodetector;
(iii) a light path between the light source and the photodetector;
(iv) a light transmissive container;
(v) a support for holding the light transmissive container in the light path between the light source and the photodetector;
(vi) a controllable heater for maintaining a liquid test mixture of the invention at a desired temperature selected in a temperature range of from 4° C. to 40° C.;
(vii) a controller for controlling the light source and the heater;
(viii) a processor for calculating an haematocrit value and a plasma fibrinogen content value based on a signal received from the photodetector during illumination of the container by at least one of the first or second wavelengths and a corresponding reference value; and
(ix) an interface to provide a user with the haematocrit value and the fibrinogen content value.

According to a preferred embodiment, an apparatus according to the invention further comprises:

(x) a second light transmissive container;
(xi) either at least a second support for holding the at least second light transmissive container in the light path between the light source and the photodetector, or the support holding all the light transmissive containers;
(xii-a) a controllable mean for controllably alternating the light transmissive containers in the light path defined between the light source and the photodetector, or
(xii-b) (a) at least a second light source configured to emit at least at one of:
 (1) a first wavelength ranging from 520 to 590 nanometers, and
 (2) a second wavelength ranging from 650 to 850 nanometers;
(b) at least a second photodetector, and
(c) at least a second light path between the at least second light source and the at least second photodetector.

The invention has for advantages to provide a simple, cost-effective, and extremely fast assay to determine plasma fibrinogen level of an individual, as well as haematocrit, on the only basis of a whole blood sample.

The methods and apparatus of the invention allow the assessment within minutes, in particular in less than 5 minutes, more particularly in less than 3 minutes, of coagulopathy development and bleeding risks and in the therapeutic management of bleeding based on the measure of fibrinogen level, as well as the detection of an alarming fibrinogen level.

Furthermore, the apparatus of the invention has the advantage of being transportable, in particular in an ambulance or any emergency rescue vehicle, and can even be transportable by rescuers and emergency care personnel in an appropriate way.

LEGENDS OF THE FIGURES

FIG. 1: illustrates the absorption spectrums between 500 and 800 nm obtained at 30° C. when tested whole blood is diluted ½₀ in solutions A or B of the invention (mixtures A and B).

Abscissa: Wavelengths in nm/Ordinate: Absorbance units.

Figure 2:
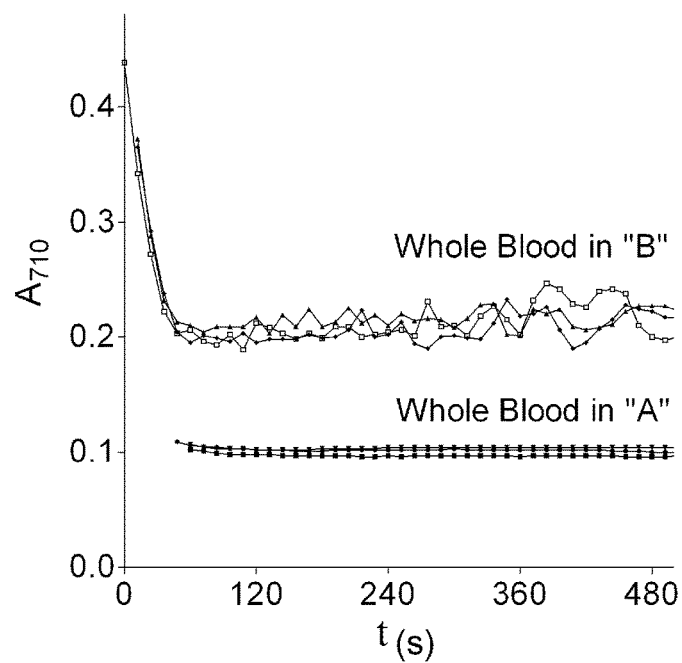

FIG. 2: illustrates the kinetic of the Absorbance at 710 nm when 190 µl of solution A or B of the invention are added to 10 µl of tested whole blood in a microplate.

Abscissa: Time (t) in seconds/Ordinate: Absorbance units at 710 nm.

Figure 3:
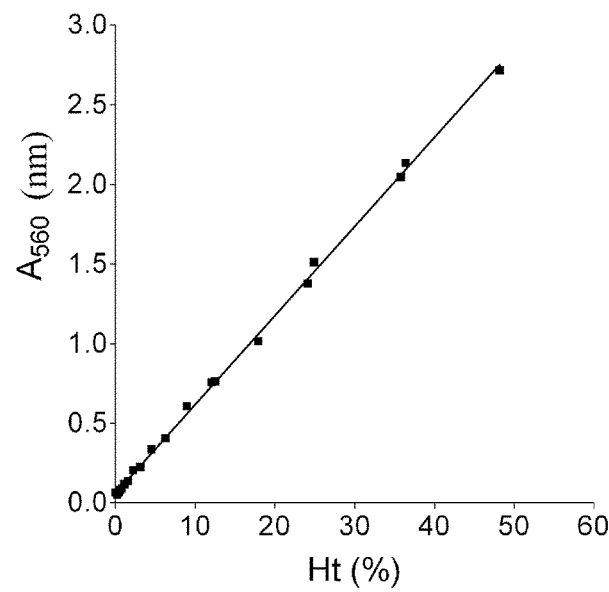

FIG. 3: illustrates a titration curve of the Absorbance at 560 nm of solution A of the invention as a function of added red blood cells (Ht, in % estimated with a standard haematologic counter).

Abscissa: Haematocrit in %/Ordinate: Absorbance units at 560 nm.

Figure 4:
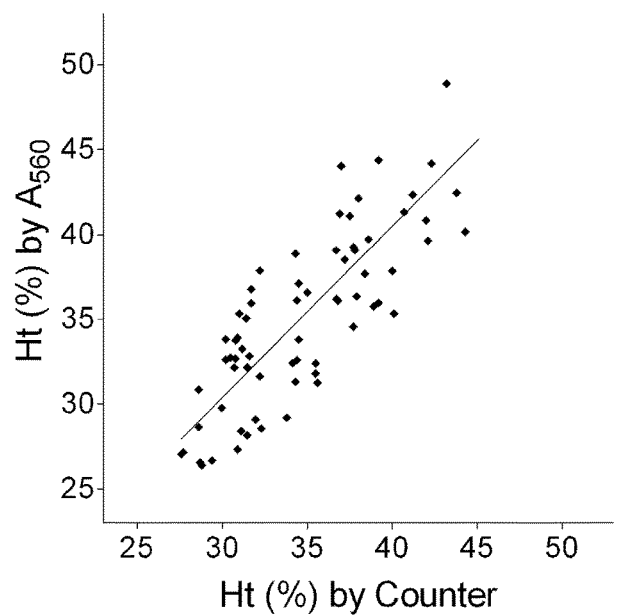

FIG. 4: illustrates a curve representing the comparison of 69 haematocrit estimates according to the POC (Point Of Care) method of the invention as a function of those provided by a standard haematologic counter.

Abscissa: Haematocrit in % determined by counter/Ordinate: Haematocrit in % determined by Absorbance at 560 nm according to a method of the invention.

Figure 5:
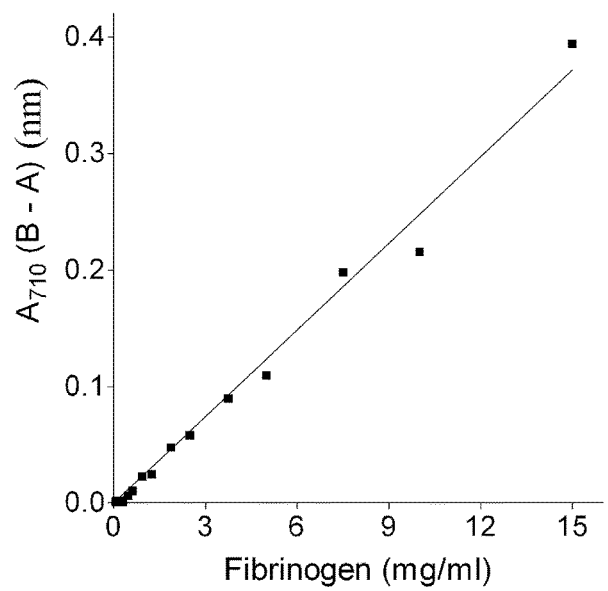

FIG. 5: illustrates a titration curve of the Absorbance at 710 nm of solution B of the invention (diminished of that of solution A of the invention) as a function of added incremental amounts of purified fibrinogen.

Abscissa: Fibrinogen content in mg/ml/Ordinate: Absorbance units at 710 nm of test solution B when deducting absorbance units at 710 nm of test solution A according to the invention.

Figure 6:
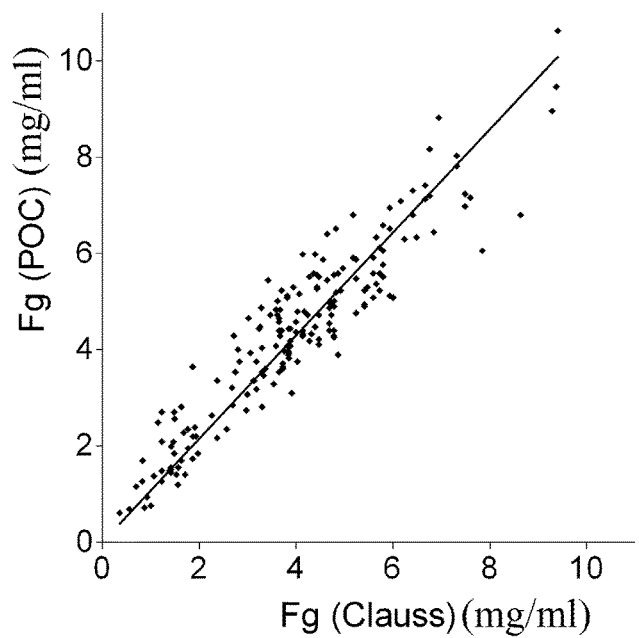

FIG. 6: illustrates a curve representing the comparison of 190 plasma samples estimates according to the POC (Point Of Care) method of the invention as a function of the fibrinogen content estimated by the reference Clauss method.

Abscissa: Fibrinogen content in mg/ml determined by Clauss' method/Ordinate: Fibrinogen content in mg/ml determined by a POC method of the invention.

Figure 7:
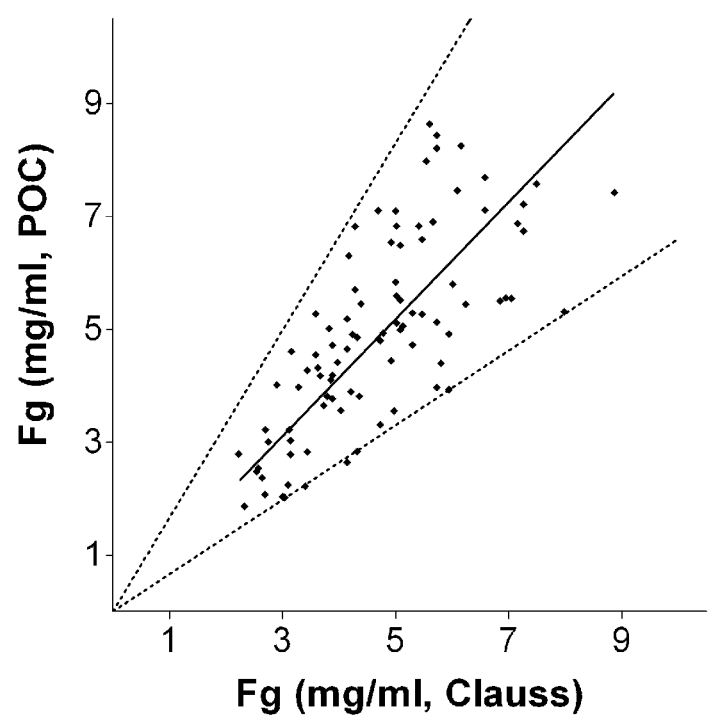

FIG. 7: illustrates a curve representing the comparison of 91 whole blood samples extrapolated to plasma equivalent estimated according to the POC (Point Of Care) method of the invention as a function of the fibrinogen content estimated by the reference Clauss method.

Abscissa: Fibrinogen content in mg/ml determined by Clauss' method/Ordinate: Fibrinogen content in mg/ml determined by a POC method of the invention.

DESCRIPTION OF THE INVENTION

Methods

The methods of the invention are based on the use of one or more whole blood sample(s) collected from an individual.

The main difference between the two method embodiments disclosed herein is the following:
a) in the first disclosed method, the haematocrit and the fibrinogen content value are both determined using the same whole blood sample, whereas
b) in the second disclosed method, the haematocrit and the fibrinogen content values, respectively, are determined using two separate whole blood samples from the same individual.

Whole Blood Sample

A whole blood sample may be collected in many known ways, but is preferentially simply collected by finger prick.

Considering the objective of the present invention, the collection of the whole blood sample does preferably not occur more than few minutes before being used in a method according to the invention. Advantageously, the whole blood sample(s) is/are collected and step (i) of the firstly disclosed method or steps (i-a) and (ii-a) of the secondly disclosed method are performed.

Steps (i), (i-a) and (ii-a) of the Methods

A given volume of whole blood sample is mixed in a liquid solution of the invention, defined hereafter, in order to obtain a test mixture.

A whole blood sample is diluted in a test mixture of the invention at least at ½0 v/v, preferably at ¼0 v/v or more.

In steps (i-a) and (ii-a), the two collected blood samples are independently diluted at ½0 v/v or more, preferably at ¼0 v/v. In a preferred way, they are both identically diluted.

A given volume of a whole blood sample according to the invention represents a volume of at least 1 μL, and in particular comprised between 1 μL and 20 μL, and preferably between 2 μL and 15 μL. In a preferred embodiment, a given volume of a whole blood sample of the invention is about 10 μL. In another embodiment, a given volume of a whole blood sample of the invention is about 5 μL.

A liquid solution of the invention into which a whole blood sample is diluted comprises a low ionic strength buffer.

In the present invention, lysis of the red blood cells is necessary for two reasons. The first one is the measure of the haematocrit which is performed with haemoglobin present in the red blood cells. The second one is to allow the detection of the fibrinogen precipitate.

A liquid solution of the invention comprises as lysis buffer a low ionic strength buffer. This buffer preferably has a pH ranging from 6.0 to 8.5. In a preferred embodiment, buffer has a pH of 7.5.

A low ionic strength buffer of the invention preferably has an ionic strength lower than 100 mM.

In a preferred embodiment of the invention, a low ionic strength buffer of the invention is selected from the group consisting of tris-HCl or HEPES, containing or not EDTA, and mixtures thereof.

In steps (i-a) and (ii-a), the low ionic strength buffers of the two liquid solutions is selected independently. The low ionic strength buffer of the two liquid solutions can thus be identical or different.

In a preferred embodiment, a low ionic strength buffer of the invention is selected among Tris-HCl buffer (50 mM, pH 7.5 without NaCl) and HEPES buffer (50 mM, pH 7.5 without NaCl).

A liquid solution of the invention further comprises at least a precipitant, this precipitant being selected from the group consisting of a $(C_1-C_6)$alcohol, acetaldehyde, acetic acid, acetone, acetonitrile, 2-butoxyethanol, butyric acid, diethanolamine, diethylenetriamine, dimethylformamide, dimethoxyethane, dimethyl sulfoxide, 1,4-dioxane, ethylamine, ethylene glycol, formic acid, furfuryl alcohol, methyl diethanolamine, methyl isocyanide, propanoic acid, pyridine and tetrahydrofuran.

The precipitant is present in step (i) of the method in a range of from 0.5 to 40% by weight, preferably 10 to 40% by weight, more particularly 20 to 40% by weight, based on the total weight of the solution.

The precipitant is present in step (i-a) of the method in a range of from 0.5 to 20% by weight, preferably 1 to 15% by weight, more preferably 10% by weight, based on the total weight of the solution.

The precipitant is present in step (i) of the method in a range of from 20 to 40% by weight, preferably 30% by weight, based on the total weight of the solution.

In a preferred embodiment, the precipitant is a $(C_1-C_6)$ alcohol or mixtures thereof.

A $(C_1-C_6)$alcohol according to the invention can more particularly be selected from the group consisting of methanol, ethanol, 1-propanol, 2-propanol, propylene glycol, 1,3-propanediol, glycerol, 1,2-butanediol, 1,3-butanediol, 1,4-butanediol and 1,5-pentanediol.

A $(C_1-C_6)$alcohol according to the invention is preferably a $(C_1-C_3)$alcohol, more preferably as defined here-above, more particularly selected from the group consisting of methanol and ethanol, and is preferably ethanol.

In a preferred embodiment, in step (i), the precipitant is a ($C_1$-$C_6$)alcohol, preferably a ($C_1$-$C_3$)alcohol, more preferably ethanol, in a content ranging from 10 to 40% by weight based on the total weight of the solution.

In a preferred embodiment, in step (i-a), the precipitant is a ($C_1$-$C_6$)alcohol, preferably a ($C_1$-$C_3$)alcohol, more preferably ethanol, in a content ranging from 1 to 20% by weight based on the total weight of the solution, and is more preferably 10% by weight.

This content in precipitant, combined with a desired temperature selected in a temperature range of from 4 to 40° C., and in particular 30° C., allows lysing all the blood cells within a minute whereas fibrinogen precipitation takes hours.

In a preferred embodiment, in step (ii-a), the precipitant is a ($C_1$-$C_6$)alcohol, preferably a ($C_1$-$C_3$)alcohol, more preferably ethanol, in a content ranging from 20 to 40% by weight based on the total weight of the solution, and is preferably 30% by weight.

This content in precipitant, combined with a desired temperature selected in a temperature range of from 4 to 40° C., and in particular 30° C., allows lysing all the blood cells within 2 minutes whereas fibrinogen precipitation is also completed in less than 2 minutes.

As indicated previously, a liquid solution according to the invention is maintained at a desired temperature, the desired temperature being selected in a temperature range of from 4 to 40° C.

In a preferred embodiment, the desired temperature is in a range of from 20 to 40° C., in particular of from 25 to 35° C., and is preferably 30° C.

In steps (i-a) and (ii-a), the desired temperature of the first and second liquid solutions is independently selected in the above indicated temperature range. Thus, the desired temperature of the two liquid solutions is either different or identical.

A liquid solution of the invention is mixed with a whole blood sample, the result being a test mixture in step (i), a first test mixture in step (i-a) and a second test mixture in step (ii-a).

Steps (ii) and (iii-a) of the Methods

A test mixture of the invention is incubated during 30 seconds or more at a desired temperature according to the invention. The incubation more particularly lasts between 30 seconds and 240 seconds, in particular between 40 seconds and 180 seconds, preferably between 60 seconds and 120 seconds.

The desired temperature of the incubation, and thus the temperature of the test mixture(s) of the invention can be different from the desired temperature of the liquid solution(s) but is preferably the same.

Steps (iii), (iv), (iv-a) and (v-a) of the Methods

After incubation, light absorbance of a test mixture of the invention is measured at different wavelengths.

In steps (iii) and (iv), a single test mixture is used after incubation for measuring light absorbance. The test mixture's absorbance is measured:

step (iii) at a wavelength ranging from 520 to 590 nanometers, preferably at a wavelength of 560 nanometers, whereby an absorbance value A is obtained; and step (iv) at a wavelength ranging from 650 to 850 nanometers, preferably at a wavelength of 710 nanometers, whereby an absorbance value B is obtained.

In steps (iv-a) and (v-a), a first and a second test mixture are independently used after incubation for measuring light absorbance.

A first test mixture's absorbance is measured at a wavelength ranging from 520 to 590 nanometers, preferably at a wavelength of 560 nanometers, whereby an absorbance value A is obtained; and a second test mixture's absorbance is measured at a wavelength ranging from 650 to 850 nanometers, preferably at a wavelength of 710 nanometers, whereby an absorbance value B is obtained.

All the measurement of absorbance values A and B of the invention are performed at a desired temperature, this desired temperature being as defined previously. This desired temperature can be similar or different from the one of the incubation step and/or of the liquid solution of the invention. The desired temperature of the measurements of absorbance value A and of absorbance value B can be similar or different.

The desired temperature of steps (iv-a) and (v-a) are identical or different, but is preferably identical.

In a preferred embodiment, the desired temperature of all the liquid solution or liquid solutions, incubation and absorbance values A and B of a method of the invention are performed at the same desired temperature, this desired temperature preferably being 30° C.

Steps (v) and (vi-a) of the Methods

In a method of the invention, the absorbance value A is compared to a haematocrit reference value or curve in order to determine the haematocrit of the tested individual. The absorbance value A is caused by the release of haemoglobin following the disruption of red blood cells. A strong correlation indeed exists between haemoglobin and haematocrit contents (Nijboer et al., J Trauma. 2007; 62(5):1310-2).

A haematocrit reference value can be established as well known in the prior art, for example by using know incremental amounts of red blood cells or haemoglobin and determining their absorbance value at a given wavelength, then reporting it on a graphic to obtain a reference curve. The ordinate can represent optical densities at a given wavelength with the abscissa representing haematocrit in percentage.

Steps (vi) and (vii-a) of the Methods

In a method of the invention, the absorbance value B is compared to a fibrinogen content reference curve in order to determine the fibrinogen content value. This value represents the fibrinogen content in whole blood, not in plasma.

As indicated previously, in a preferred embodiment, a method of the invention preferably further comprises the step of determining a fibrinogen content value in the plasma of the individual using the haematocrit value and the fibrinogen content in the whole blood determined in step.

Indeed, knowing the haematocrit, the volume of whole blood and the fibrinogen content value in whole blood provides, by cross-multiplication and, when required, the correction needed to take into account the volume of added anticoagulant (usually 10% of whole blood), the plasma fibrinogen content value.

Due to possible variations of the haematocrit in an individual, it is very advantageous to use a haematocrit value determined simultaneously to the fibrinogen content in whole blood for the conversion into conventional fibrinogen content in plasma, rather than a pre-fixed general haematocrit value. This indeed provides with a more accurate information on fibrinogen content value.

A fibrinogen content reference value can be established as well known in the prior art, for example by using know incremental amounts of fibrinogen and determining their absorbance value at a given wavelength, then reporting it on a graphic to obtain a reference curve. The ordinate can represent optical densities at a given wavelength with the abscissa representing fibrinogen content, in mg/ml for example, in whole blood or in plasma.

Depending of the specie of the individual tested, the haematocrit and fibrinogen reference values can be adapted accordingly.

A method according to the invention allows to obtain information as an intermediate result rather than to obtain the diagnostic results or else condition. The results obtained through a method of the invention.

A method of the invention provides rescuers and emergency care personnel reliable and very fast information on the whole blood or plasma fibrinogen content and on the haematocrit of an individual. Rescuers and emergency care personnel can then use this information to determine different diagnosis and adapted treatments.

Apparatus

As indicated previously, the present invention concerns an apparatus for determining both (i) the haematocrit value and (ii) the fibrinogen content value in whole blood of an individual, comprising:
  (i) a light source configured to emit at least at one of:
    (1) a first wavelength ranging from 520 to 590 nanometers, and
    (2) a second wavelength ranging from 650 to 850 nanometers;
  (ii) a photodetector;
  (iii) a light path between the light source and the photodetector;
  (iv) a light transmissive container;
  (v) a support for holding the light transmissive container in the light path between the light source and the photodetector;
  (vi) a controllable heater for maintaining a liquid test mixture as defined previously at a desired temperature selected in a temperature range of from 4° C. to 40° C.;
  (vii) a controller for controlling the light source and the heater;
  (viii) a processor for calculating an haematocrit value and a plasma fibrinogen content value based on a signal received from the photodetector during illumination of the container by at least one of the first or second wavelengths and a corresponding reference value; and
  (ix) an interface to provide a user with the haematocrit value and the fibrinogen content value.

The desired temperature is as defined previously and is preferably of 30° C.

An interface of the apparatus according to the invention can for example be a speaker, a video screen, a printer or a hologram generator.

In an embodiment, the whole blood sample is directly added into the light transmissive container, in which a liquid solution according to the invention is already present or is added after addition of the whole blood sample. Preferably, the whole blood sample is added into the light transmissive container after or concomitantly or mixed with the liquid solution.

In another embodiment, the apparatus of the invention advantageously further comprises a controllable whole blood collector, the collector allowing to collect a selected volume of whole blood sample of an individual.

The controllable whole blood collector can for example be a needle combined with a suction mean.

An apparatus of the invention can further comprise a duct having an inlet connected to the controllable whole blood collector and an outlet connected to the light transmissive container.

In an embodiment, the controller (vii) is also for controlling the controllable whole blood collector.

Furthermore, in a preferred embodiment, an apparatus of the invention further comprises:
  a first duct having an inlet connected to a controllable whole blood collector of the invention, and an outlet connected to a first container, and
  a second duct having an inlet connected to the first container, and an outlet connected to the light transmissive container,
  the first container being for mixing at least the collected whole blood sample and a liquid solution of the invention in order to generate a test mixture.

In a particular embodiment, the internal volume of the first container and/or of the light transmissive container can be controllably reduced and/or increased using at least one controllable mean. This controllable mean can for example be a controllable plunger In an embodiment, the controller (vii) is also for controlling a controllable mean for varying the internal volume of the first container and/or of the light transmissive container.

According to a preferred embodiment, an apparatus according to the invention further comprises:
  (x) a second light transmissive container;
  (xi) either at least a second support for holding the at least second light transmissive container in the light path between the light source and the photodetector, or the support holding all the light transmissive containers;
  (xii-a) a controllable mean for controllably alternating the light transmissive containers in the light path defined between the light source and the photodetector, or
  (xii-b) (a) at least a second light source configured to emit at least at one of:
    (1) a first wavelength ranging from 520 to 590 nanometers, and
    (2) a second wavelength ranging from 650 to 850 nanometers;
  (b) at least a second photodetector, and
  (c) at least a second light path between the at least second light source and the at least second photodetector.

An apparatus according to this embodiment can for example be used for performing a method according to the second embodiment disclosed here-above.

According to this embodiment, an apparatus of the invention can further comprise two ducts, both having an inlet connected to a controllable whole blood collector and one having an outlet connected to a first light transmissive container, the other having an outlet connected to a second light transmissive container.

According to a preferred embodiment, an apparatus of the invention further comprises:
  two first ducts, both having an inlet connected to a controllable whole blood collector and one having an outlet connected to a first container, the other having an outlet connected to a second container,
  a third duct having an inlet connected to the first container, and an outlet connected to a first light transmissive container, and
  a fourth duct having an inlet connected to the second container, and an outlet connected to a second light transmissive container, the first and second containers being for mixing at least the collected whole blood samples and liquid solutions of the invention in order to generate test mixtures.

According to an embodiment, containers according to the invention are disposable.

According to an embodiment, an apparatus of the invention can further comprise an artificial intelligence for generating a recommendation according to the haematocrit value determined and/or to the fibrinogen content value.

An apparatus according to the invention is relatively cheap and necessitates a low quantity of material.

Thus, an apparatus according to the invention is advantageously handheld.

The examples presented hereafter are for illustrating purpose of the invention and should not be construed as limiting the scope of the invention.

EXAMPLES

Example 1

Determination of the Absorption Spectrums Between 500 and 800 nm when Diluting a Whole Blood Sample in Solutions of the Invention 1—Materials and Methods Two liquid solutions (A and B) have firstly been prepared as indicated hereafter.

Solution A:

Tris-HCL buffer (50 mM, pH 7.5) containing 10% of ethanol.

Solution B:

Hepes buffer (50 mM, pH 7.5) containing 30% of ethanol.

Then, 10 µl of a whole blood sample is mixed to 190 µl of either solution A or B in order to be diluted 1/20, at 30° C., respectively forming mixtures A and B. The two mixtures obtained are then incubated at 30° C. for 90 seconds.

Then, the absorbance between 500 and 800 nm (5 nm step) of the two mixtures are recorded in a MWG Discovery HT-R microplate reader thermostated at 30° C. piloted through the KC4 computer software (Biotek).

The variation of the absorbances at 560 nm and 710 nm of the two mixtures are recorded over time. This experiment is repeated 2 more times starting from the same sample of whole blood.

2—Results

As it appears from FIG. 1, two peaks centered at 541 nm and 577 nm can be observed, corresponding to oxyhaemoglobin, and the peaks overlap at 560 near the unique peak of de-oxyhaemoglobin centered at 555 nm.

The absorbance at 560 nm ($A_{560}$) of mixture A constitutes an adequate averaging proportional to the total haemoglobin content using the published (van Kampen et al., Adv Clin Chem. 1983; 23:199-257) molar extinction coefficient (13.1 $L \cdot mM^{-1} \cdot cm^{-1}$).

On the contrary, the higher turbidity at $A_{560}$ of mixture B due to the precipitation of fibrinogen renders it less reliable to determine said haemoglobin content unless a correction is applied. The said correction is conveniently obtained by subtracting from the $A_{560}$ of mixture B the turbidity given by the absorbance at 710 nm of the same mixture B.

a) $A_{710}$ Kinetic

It can be seen in FIG. 2 a decrease of the absorbance during the first 60 seconds of the absorbance measurement at 710 nm ($A_{710}$) for mixture B, which is linked to the lysis of the red blood cells. Absorbance is then stable for at least 8 minutes.

The three curves represent three repeats of the same experiment.

b) $A_{560}$ Kinetic

The kinetic observed at $A_{560}$ is similar to the one observed at 710 nm as indicated in FIG. 2 except that the values are comprised between 1.5 and 3.0 absorbance units, as it can be seen in FIG. 1.

Example 2

Establishment of a Titration Curve of the $A_{560}$ of Mixture A as a Function of Added Red Blood Cells (Haematocrit)

1—Materials and Methods

A liquid solution A has firstly been prepared as in Example 1.

A serial dilution of packed red blood cells is done in the homologous plasma.

Then, 10 µl of each dilution is mixed to 190 µl of solution A in order to be diluted 1/20, at 30° C. forming mixtures A. The mixture obtained is then incubated at 30° C. for 90 seconds at 30° C.

Then, the $A_{560}$ nm is recorded in a microplate reader as in Example 1.

2—Results

The curve obtained (see FIG. 3) reveals the linear relationship between the concentration of haemoglobin released in mixture A from the red blood cells and the resulting $A_{560}$ ($p<0.0001$; $r^2>0.99$).

Number of red blood cells, or more precisely the volume occupied by red blood cells, is proportional to the haemoglobin content.

Consequently, knowing the amount of haemoglobin in a sample permits to assess the number of blood cells and therefore the initial haematocrit.

Standard relationship is haemoglobin (g/dL) equal 1/3.16 haematocrit (%).

Example 3

Comparison of 69 Haematocrit Estimates According to a Method of the Invention as a Function of Those Provided by a Standard Haematologic Counter 1—Materials and Methods $A_{560}$ of 69 mixtures A obtained according to Example 1 with 69 different 10 µl blood samples obtained through a daily clinical care protocol (Hôtel Dieu and Cochin Hospitals) were recorded at 30° C. and haematocrit (%) determined according to the titration curve of Example 2.

Then, the values obtained were compared with those provided by the hospital determined according to a standard haematologic counter (Sysmex XE and XT, Villepinte, France) in order to evaluate the reliability of the method of the invention.

2—Results

The resulting curve (see FIG. 4—p lower than 0.0001 and $r^2=0.69$) is not as satisfactory as that obtained through serial dilution of packed red blood cells, but it can be noted that the standard error is less than 15% and thus that the uncertainty introduced by the method of the invention is acceptable with respect to the purpose of said method, i.e. rapid, on site, and for the detection of threatening levels of haematocrit and fibrinogen.

Example 4

Establishment of a Titration Curve of the $A_{710}$ of Mixture B as a Function of Added Fibrinogen 1—Materials and Methods 10 µL of known incremental concentrations of purified fibrinogen were diluted in above-indicated mixtures A and B at 30° C.

90 seconds after mixing, the $A_{710}$ of each mixture is recorded every 12 seconds for a period of one minute.

Turbidity resulting from fibrinogen precipitation was estimated by subtracting from the average $A_{710}$ of mixture B that of the average $A_{710}$ of mixture A.

2—Results

The curve obtained (see FIG. 5) suggests that, at least up to 15 mg/ml, a linear relationship exists between the initial amount of fibrinogen and the turbidity increased measured at 710 nm in solution B subtracted from that in mixture A ($p<0.0001$; $r^2>0.98$).

Thus, knowing the $A_{710}$ of mixtures A and B permits assessing the turbidity increase and thus the initial amount of fibrinogen contained in a sample. A simple coefficient then allows transforming this $A_{710}$ into a fibrinogen amount.

Example 5

Comparison of 190 Fibrinogen Contents in Plasma Samples (Mg/Ml) Estimated According to a Method of the Invention as a Function of the Fibrinogen Contents Estimated by the Reference Clauss Method 1—Materials and Methods Absorbance at 710 nm of 190 mixtures A and B obtained according to example 1 with 190 different 10 µl plasma samples were recorded at 30° C. and fibrinogen content (mg/ml) determined according to the titration curve of example 4.

Fibrinogen content was computed from the turbidity using 46.0 as the coefficient to transcribe into mg/ml the differences of $A_{710}$ in mixture A from that in mixture B.

2—Results

Pending that precise quantity of plasma is added and that temperature is finely regulated, results indicate an acceptable correlation ($p<0.0001$ and $r^2=0.88$) with the fibrinogen level measured through the Clauss method (see FIG. 6).

The amount of fibrinogen in whole blood is however not directly proportional to that in plasma (Amukele et al., 2010). Indeed, haematocrit varies between 25 and 60%, and thus the amount of fibrinogen measured in whole blood should preferentially be corrected according to the haematocrit, through a simple cross multiplication, to be comparable to an estimate in plasma.

Example 6

Comparison of 91 Fibrinogen Contents in Whole Blood Samples (Mg/Ml) Extrapolated to Plasma Equivalent Estimated According to a Method of the Invention as a Function of the Fibrinogen Contents Estimated in Plasma by the Reference Clauss Method 1—Materials and Methods $A_{710}$ of 91 mixtures A and B obtained according to Example 1 with 91 different 10 µl whole blood samples were recorded at 30° C. and fibrinogen content (mg/ml) determined according to the titration curve of example 4.

Fibrinogen content was computed as indicated in example 5.

Moreover, haematocrit was deduced from the $A_{560}$ of mixture A and used to transcribe the fibrinogen content estimate in whole blood into its plasma equivalent through cross multiplication.

2—Results

While goodness of fit still exhibits $p<0.0001$, the $r^2$ drops to 0.53 (see FIG. 7). Correlation is thus not as satisfactory as the one obtained with plasma in example 5.

It appears however that error is a function of the fibrinogen concentration (proportional error) suggesting that uncertainty introduced by the method of the invention is acceptable with respect to the purpose of said method, i.e. rapid, on site, and for the detection of threatening levels of haematocrit and fibrinogen.

Example 7

Determination of the Absorption Spectrums Between 500 and 800 nm when Diluting a Whole Blood Sample in a Solution of the Invention 1—Materials and Methods A liquid solution (C) has firstly been prepared as indicated hereafter:

Solution C:

Hepes buffer (50 mM, pH 7.5) containing 30% of ethanol.

Then, 10 µl of a sample of the same whole blood as the one used in example 1 is mixed to 190 µl of solution C in order to be diluted ½0, at 30° C., forming mixture C. The mixture obtained is then incubated at 30° C. for 90 seconds.

Then, the absorbance between 500 and 800 nm (5 nm step) of mixture C is recorded as proceeded in example 1 with mixtures A and B.

The variation of the absorbances at 560 nm and at 710 nm of mixture C is recorded over time. This experiment is repeated 2 more times starting from the same sample of whole blood.

2—Results

The same curve as the one obtained with mixture B in FIG. 1 is obtained.

Haematocrit (%) is determined according to the titration curve of Example 2 as indicated in example 3.

In order to obtain a more precise measure of the $A_{560}$, slightly higher than it should be due to the turbidity introduced by the precipitation of fibrinogen, a correction can be applied. The said correction consists in subtracting from the $A_{560}$ of mixture C the turbidity given by the absorbance at 710 nm of the same mixture C.

Haematocrit (%) is then also determined according to the titration curve of Example 2 as indicated in example 3 and provides an advantageously slightly more accurate result than the one obtained without the correction.

The fibrinogen content (mg/ml) is determined according to the titration curve of example 4 as indicated in examples 5 and 6 except that a universal background value of 0.052 absorbance unit is deduced from each $A_{710}$ measurement before the computing.

Haematocrit determined above is used to transcribe the fibrinogen content estimate in whole blood into its plasma equivalent through cross multiplication.

The results obtained indicate an acceptable correlation with the fibrinogen level measured through the Clauss method.

All these tests were performed by using blood samples stored up to several hours following collection before testing. Thus, when using a whole blood sample directly from a fingertip, as it is not necessary to resuspend said sample, the results obtained are improved.

The invention claimed is:

1. A method for determining both (a) the haematocrit value and (b) the fibrinogen content in whole blood of an individual comprising:
   (i) mixing a given volume of whole blood sample from the individual with a liquid solution, wherein the liquid solution comprises a low ionic strength buffer as well as a precipitant, and wherein the content of the precipitant ranges from 0.5 to 40% by weight based on the total weight of the solution, whereby a test mixture is obtained,
   the precipitant being selected from the group consisting of a $(C_1-C_6)$alcohol, acetaldehyde, acetic acid, acetone, acetonitrile, 2-butoxyethanol, butyric acid, diethanolamine, diethylenetriamine, dimethylformamide, dimethoxyethane, dimethyl sulfoxide, 1,4-dioxane, ethylamine, ethylene glycol, formic acid, furfuryl alcohol, methyl diethanolamine, methyl isocyanide, propanoic acid, pyridine and tetrahydrofuran,
   the low ionic strength buffer having an ionic strength lower than 100 mM;
   (ii) incubating the test mixture for 30 seconds or more;
   (iii) measuring light absorbance of the test mixture obtained at the end of step (ii) at a wavelength ranging from 520 to 590 nanometers whereby an absorbance value A is obtained;
   (iv) measuring light absorbance of the test mixture obtained at the end of step (ii) at a wavelength ranging from 650 to 850 nanometers, whereby an absorbance value B is obtained;
   (v) determining the haematocrit value of the individual by comparing the absorbance value A obtained at step (iii) with an haematocrit reference value; and
   (vi) determining the fibrinogen content in the whole blood of the individual by comparing the absorbance value B obtained at step (iv) with a fibrinogen content reference value;
   wherein the liquid solution used at step (i) and the test mixture used at steps (ii) to (iv) are maintained at a desired temperature, the desired temperature being selected in a temperature range of from 4 to 40° C.

2. The method according to claim 1, wherein the precipitant is a $(C_1-C_6)$alcohol or mixtures thereof.

3. The method according to claim 1, wherein the absorbance value A is measured at step (iii) at a wavelength of 560 nanometers.

4. The method according to claim 1, wherein the absorbance value B is measured at step (iv) at a wavelength of 710 nanometers.

5. The method according to claim 1, wherein the desired temperature is in a range of from 20 to 40° C.

6. A method for determining both (a) the haematocrit value and (b) the fibrinogen content in whole blood of an individual comprising the steps of:
   (i-a) mixing a given volume of a first whole blood sample from an individual with a first liquid solution, wherein the first liquid solution comprises a low ionic strength buffer as well as a precipitant, and wherein the content of the precipitant ranges from 0.5 to 20% by weight based on the total weight of the solution, whereby a first test mixture is obtained,
   the precipitant being selected from the group consisting of a $(C_1-C_6)$alcohol, acetaldehyde, acetic acid, acetone, acetonitrile, 2-butoxyethanol, butyric acid, diethanolamine, diethylenetriamine, dimethylformamide, dimethoxyethane, dimethyl sulfoxide, 1,4-dioxane, ethylamine, ethylene glycol, formic acid, furfuryl alcohol, methyl diethanolamine, methyl isocyanide, propanoic acid, pyridine and tetrahydrofuran,
   the low ionic strength buffer having an ionic strength lower than 100 mM;
   (ii-a) mixing another given volume of a second whole blood sample from the individual with a second liquid solution, wherein the second liquid solution comprises a low ionic strength buffer as well as a precipitant, and wherein the content of the precipitant ranges from 20 to 40% by weight based on the total weight of the solution, whereby a second test mixture is obtained,
   the precipitant being selected from the group consisting of a $(C_1-C_6)$alcohol, acetaldehyde, acetic acid, acetone, acetonitrile, 2-butoxyethanol, butyric acid, diethanolamine, diethylenetriamine, dimethylformamide, dimethoxyethane, dimethyl sulfoxide, 1,4-dioxane, ethylamine, ethylene glycol, formic acid, furfuryl alcohol, methyl diethanolamine, methyl isocyanide, propanoic acid, pyridine and tetrahydrofuran,
   the low ionic strength buffer having an ionic strength lower than 100 mM;
   (iii-a) incubating the first and second test mixtures for 30 seconds or more;
   (iv-a) measuring light absorbance of the first test mixture obtained at the end of step (iii-a) at a wavelength ranging from 520 to 590 nanometers, whereby an absorbance value A is obtained;
   (v-a) measuring light absorbance of the second test mixture obtained at the end of step (iii-a) at a wavelength ranging from 650 to 850 nanometers, whereby an absorbance value B is obtained;
   (vi-a) determining the haematocrit value of the individual by comparing the absorbance value A obtained at step (iv-a) with an haematocrit reference value; and
   (vii-a) determining the fibrinogen content in the whole blood of the individual by comparing the absorbance value B obtained at step (v-a) with fibrinogen content reference value;
   wherein the first and second liquid solutions used at steps (i-a) and (ii-a) and the first and second test mixtures used at steps (iii-a) to (v-a) are each independently maintained at a desired temperature, the desired temperature being selected in a temperature range of from 4 to 40° C.

7. The method according to claim 6, wherein the precipitant of steps (i-a) and (ii-a) is, independently, a $(C_1-C_6)$alcohol.

8. The method according to claim 6, wherein the light absorbance of the first test mixture is measured in step (iv-a) at a wavelength of 560 nanometers.

9. The method according to claim 6, wherein the light absorbance of the second test mixture is measured in step (v-a) at a wavelength of 710 nanometers.

10. The method according to claim 6, wherein the first liquid solution comprises ethanol in a content of 10% by weight based on the total weight of the solution and the desired temperature is in a range of from 25 to 35° C.

11. The method according to claim 6, wherein the second liquid solution comprises ethanol in a content of 30% by weight based on the total weight of the solution and the desired temperature is in a range of from 25 to 35° C.

12. The method according to claim 6, further comprising the following step:
(viii-a) determining a fibrinogen content value in the plasma of the individual using the haematocrit value obtained at step (vi-a) and the fibrinogen content in the whole blood determined at step (vii-a).

* * * * *